(12) United States Patent
Nomura et al.

(10) Patent No.: US 6,303,624 B1
(45) Date of Patent: Oct. 16, 2001

(54) PREVENTIVES AND REMEDIES FOR HYPERPHOSPHATEMIA

(75) Inventors: Kazuhiko Nomura, Takatsuki; Emiko Sasaki; Kazumi Nakazi, both of Osaka; Tokuaki Kajiho, Kobe, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/380,617

(22) PCT Filed: Mar. 5, 1998

(86) PCT No.: PCT/JP98/00933

§ 371 Date: Nov. 4, 1999

§ 102(e) Date: Nov. 4, 1999

(87) PCT Pub. No.: WO98/41237

PCT Pub. Date: Sep. 24, 1998

(30) Foreign Application Priority Data

Mar. 18, 1997 (JP) .................................................. 9-064034

(51) Int. Cl.$^7$ .................. A61K 31/4162; A61K 31/437; A61P 5/18
(52) U.S. Cl. ............................................ 514/300; 514/403
(58) Field of Search .................................... 514/283, 300, 514/403; 546/121

(56) References Cited

U.S. PATENT DOCUMENTS

| 4,925,849 | 5/1990 | Shiokawa et al. | 514/300 |
| 4,985,444 | 1/1991 | Shiokawa et al. | 514/300 |
| 5,204,346 | 4/1993 | Shiokawa et al. | 514/234.5 |
| 5,234,930 | 8/1993 | Shiokawa et al. | 514/300 |
| 5,338,743 | 8/1994 | Shiokawa et al. | 514/300 |
| 5,643,938 | 7/1997 | Kohno et al. | 514/403 |
| 5,773,530 | 6/1998 | Akahane et al. | 544/238 |

FOREIGN PATENT DOCUMENTS

WO 93/25205 * 12/1993 (JP) .
WO 95/18128 * 7/1995 (JP) .

* cited by examiner

*Primary Examiner*—Edward J. Werman
*Assistant Examiner*—Helen Nguyen
(74) *Attorney, Agent, or Firm*—Oblon, Spivak, McClelland, Maier & Neustadt, P.C.

(57) ABSTRACT

This invention has for its object to provide a pharmaceutical composition for the prevention and/or treatment of hyperphosphatemia and secondary hyperparathyroidism, inclusive of their accessory disorders and symptoms.

The object is accomplished by provision of a pharmaceutical composition comprising an adenosine antagonist as an active ingredient.

10 Claims, No Drawings

PREVENTIVES AND REMEDIES FOR HYPERPHOSPHATEMIA

TECHNICAL FIELD

The present invention relates to a pharmaceutical composition for the prevention and/or treatment of hyperphosphatemia which comprises an adenosine antagonist compound or a salt thereof as an active ingredient and so is useful in the pharmaceutical field.

BACKGROUND ART

In the treatment of hyperphosphatemia, calcium preparations are in broad use today.

Calcium preparations have the drawback that they induce hypercalcemia to promote ectopic calcification, which imposes limits on their dosage. As an additional disadvantage, those preparations inhibit absorption of iron to encourage progression of renal anemia.

In the medical scene, a drug which is free from these defect and effective for the treatment of hyperphosphatemia is demanded, and this invention has for its object to fulfill this need.

DISCLOSURE OF INVENTION

The inventors of the present invention discovered for the first time that antagonists of adenosine receptors are effective in preventing and/or treating hyperphosphatemia and secondary hyperparathyroidism, inclusive of their accessory disorders and symptoms, and have accordingly developed this instant invention. The present invention, therefore, accomplishes the above object by providing a pharmaceutical composition comprising an adenosine antagonist compound or a salt thereof as its active ingredient.

The present invention is carried into practice by administering an adenosine antagonist compound or a salt thereof, or a pharmaceutical composition containing an adenosine antagonist or a salt thereof as an active ingredient, to a human being or an animal.

The term "adenosine antagonist" is used herein to mean a substance which opposes adenosine in the binding to the receptors of adenosine, and many substances of this kind are known and generally subsumed in the concept of "adenosine antagonist" by any one skilled in the art.

In the present invention, such an adenosine antagonist is used as the active ingredient but the preferred is an adenosine $A_1$ receptor antagonist. The term "adenosine $A_1$ antagonist" as used herein means an adenosine antagonist having a preferentially high affinity for adenosine $A_1$ receptors.

The preferred example for use in the practice of the present invention, among such adenosine $A_1$ receptor antagonists, is the pyrazolopyridine compound of the following general formula (I), or its salt.

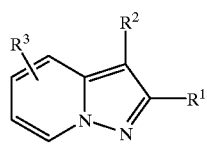

(I)

[wherein
  $R^1$ is lower alkyl, aryl which may have one or more suitable substituents or a heterocyclic group, $R^2$ is a group of the formula:

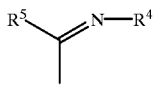

(wherein
  $R^4$ is protected amino or hydroxy, and
  $R^5$ is hydrogen or lower alkyl); cyano;
  a group of the formula:

(wherein $R^6$ is acyl, and
  A is lower aliphatic hydrocarbon group which may have one or more suitable substituents);
  amidated carboxy group;
  unsaturated heterocyclic group which may have one or more suitable substituents;
  amino; or protected amino, and
  $R^3$ is hydrogen, lower alkyl, lower alkoxy or halogen].

As specific examples of said pyrazolopyridine compound (I), those known compounds which are described in Japanese laid-open (Kokai Tokkyo Koho) No. S64-45385, H2-243689, H4-253978 and H5-112566, and WO 95/18128 can be mentioned.

Suitable salts of pyrazolopyridine compound (I) for the purposes of this invention are the conventional kinds of pharmaceutically acceptable salts, and include salts with metals such as alkali metals (e.g. sodium, potassium, etc.) or alkaline earth metals (e.g. calcium, magnesium, etc.), ammonium salts, salts with organic bases (e.g. trimethylamine, triethylamine, pyridine, picoline, dicyclohexylamine, N,N'-dibenzylethylenediamine, etc.), salts with organic acids (e.g. acetic acid, trifluoroacetic acid, maleic acid, tartaric acid, fumaric acid, methanesulfonic acid, benzenesulfonic acid, formic acid, toluenesulfonic acid, etc.), salts with inorganic acids (e.g. hydrochloric acid, hydrobromic acid, hydriodic acid, sulfuric acid, phosphoric acid, etc.), and salts with amino acids (e.g. arginine, aspartic acid, glutamic acid, etc.), etc.

In the above and following descriptions of the present specification, the various definitions falling within the scope of this invention and the preferred examples thereof as well as relevant comments are given below.

The term "lower" means 1 through 6 carbon atoms unless otherwise specified.

The term "higher" means 7 through 20 carbon atoms unless otherwise specified.

Suitable "lower aliphatic hydrocarbon group" may include the lower alkyl, lower alkenyl and lower alkinyl groups mentioned below.

Suitable "lower alkyl group" may include straight-chain or branched-chain alkyl groups such as methyl, ethyl, propyl, isopropyl, butyl, tert-butyl, pentyl and hexyl. The preferred example, among them, may be ($C_1$–$C_4$) alkyl groups and the more preferred one may be methyl, ethyl, propyl and isopropyl.

Suitable "lower alkenyl group" may include straight-chain or branched-chain alkenyl groups such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl and 5-hexenyl. The preferred example, among them, may be ($C_2$–$C_4$) alkenyl groups and the more preferred one may be vinyl, 1-methylvinyl, 2-methylvinyl and 1,3-butadienyl.

Suitable "lower alkynyl group" may include straight-chain or branched-chain alkynyl groups such as ethynyl, 1-propynyl, 1-methylethynyl, 2-butynyl, 2-methyl-3-butynyl, 2-pentynyl and 1-hexynyl. The preferred example may be ($C_2$–$C_4$) alkynyl groups and the more preferred one may be ethynyl.

The "lower aliphatic hydrocarbon group" mentioned above may have one or more, preferably 1 through 3, suitable substituents such as halogen atoms (e.g. chloro, bromo, fluoro and iodo).

Suitable "protected amino group" may include lower alkylamino groups such as methylamino, ethylamino, propylamino, butylamino, tert-butylamino, pentylamino, hexylamino, etc.; di(lower)alkylamino groups such as dimethylamino, diethylamino, N-ethylpropylamino, dibutylamino, N-(tert-butyl)pentylamino, dihexylamino, etc.; and those protected amino groups as protected with the conventional amino-protecting groups, such as the acylamino groups mentioned below.

Suitable "acylamino group" may include ureido; lower alkanoylamino groups such as formylamino, acetylamino, propionylamino, butyrylamino, isobutyrylamino, pivaloylamino, hexanoylamino, etc.; lower alkoxycarbonylamino groups such as methoxycarbonylamino, ethoxycarbonylamino, propoxycarbonylamino, tert-butoxycarbonylamino, pentyloxycarbonylamino, hexyloxycarbonylamino, etc.; lower alkoxycarbonyl(lower)alkanoylamino groups such as methoxycarbonylacetylamino, ethoxycarbonylacetylamino, 2-(propoxycarbonyl)propionylamino, 4-(tert-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc.; and lower alkanesulfonylamino groups such as methanesulfonylamino, ethanesulfonylamino, propanesulfonylamino, butanesulfonylamino, tert-butanesulfonylamino, pentanesulfonylamino, hexanesulfonylamino, etc., among others.

The "lower alkanoylamino group" mentioned above may have suitable substituents such as di(lower)alkylamino groups (e.g. dimethylamino, N-methyl-N-ethylamino, dipropylamino, di-tert-butylamino, N-pentyl-N-hexylamino, etc.) and cyclic amino groups which may have lower alkyl (e.g. piperidino etc.)etc. Suitable example of said "lower alkanoylamino group having suitable substituents" may be lower alkanoylamino groups having di(lower)alkylamino, such as dimethylaminocarbonylamino, 2-dimethylaminoacetylamino, 2-(N-methyl-N-ethylamino)acetylamino, 2-dimethylaminopropionylamino, 3-dipropylaminobutyrylamino, 2-(di-tert-butylamino)-2-methylpropionylamino, 2-dimethylaminomethyl-2-methylpropionylamino, 6-(N-pentyl-N-hexylamino)hexanoylamino, etc. and lower alkanoylamino groups having a cyclic amino group optionally having lower alkyl, such as piperidinocarbonylamino, 2-piperidinoacetylamino, 2-(2-methylpiperidino)acetylamino, 2-(2-ethylpiperidino)acetylamino, 2-piperidinopropionylamino, 3-(2-ethylpiperidino)butyrylamino, 2-(4-ethylpiperidino)-2-methylpropionylamino, 2-piperidinomethyl-2-methylpropionylamino and 6-(3-propylpiperidino)hexanoylamino, among others.

The preferred example of said "acylamino group" may be ureido, ($C_1$–$C_4$)alkanoylamino, ($C_1$–$C_4$)alkoxycarbonyl($C_1$–$C_4$)alkanoylamino, di($C_1$–$C_4$)alkylamino($C_1$–$C_4$)alkanoylamino, ($C_1$–$C_4$)alkylpiperidino($C_1$–$C_4$)alkanoylamino, ($C_1$–$C_4$)alkoxycarbonylamino, ($C_1$–$C_4$)alkanesulfonylamino, ($C_1$–$C_4$)alkylamino and di($C_1$–$C_4$)alkylamino. The preferred example, among them, may be ureido, acetylamino, 2-(ethoxycarbonyl)acetylamino, 2-dimethylaminoacetylamino, 2-(2-ethylpiperidino)acetylamino, methoxycarbonylamino, methanesulfonylamino, methylamino and dimethylamino.

Suitable "acyl group" may include lower alkanoyl groups (e.g. formyl, acetyl, propionyl, butyryl, isobutyryl, pivaloyl, hexanoyl, etc.), carboxy, protected carboxy, etc.

Suitable example of said "protected carboxy" may include esterified carboxy groups, suitable example of which may be lower alkoxycarbonyl groups (e.g. methoxycarbonyl, ethoxycarbonyl, propoxycarbonyl, butoxycarbonyl, tert-butoxycarbonyl, pentyloxycarbonyl, hexyloxycarbonyl, etc.), which may have nitrogen-containing heterocyclic group, and amidated carboxy groups such as N-(lower)alkylcarbamoyl groups such as N-methylcarbamoyl, N-ethylcarbamoyl, N-isopropylcarbamoyl, N-butylcarbamoyl, N-pentylcarbamoyl, N-hexylcarbamoyl, etc.;

N-(higher)alkylcarbamoyl groups such as N-heptylcarbamoyl, N-(2-methylheptyl)carbamoyl, N-nonylcarbamoyl, N-decanylcarbamoyl, N-tricyclo[3.3.1.1.$^{3,7}$]decanylcarbamoyl, N-undecanylcarbamoyl, N-(bicyclo[4.3.2]undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-eicosanylcarbamoyl, etc.;

N,N-di(lower)alkylcarbamoyl groups such as N,N-dimethylcarbamoyl, N,N-diethylcarbamoyl, N-methyl-N-ethylcarbamoyl, N,N-dipropylcarbamoyl, N,N-di(tert-butyl)carbamoyl, N-pentyl-N-hexylcarbamoyl, etc.;

N-(lower)alkyl-N-ar(lower)alkylcarbamoyl groups such as N-methyl-N-benzylcarbamoyl etc.; and groups of the formula:

(wherein $R_N$ is a nitrogen-containing heterocyclic group which may have one or more suitable substituents and may contain an additional hetero atom or atoms selected from among N, O and S in its rig).

Suitable "nitrogen-containing heterocyclic group" may include a variety of saturated or unsaturated monocyclic or polycyclic heterocyclic groups, for example unsaturated 3- through 8-membered (more preferably 5- through 7-membered) heteromonocyclic groups containing 1 to 4 nitrogen atoms as ring atoms, such as azepinyl (e.g. 1H-azepinyl etc.), pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.);

saturated 3- through 8-membered (more preferably 5- through 7-membered) heteromonocyclic groups containing 1 through 4 nitrogen atoms as ring atoms, such as perhydroazepinyl (e.g. perhydro-1H-azepinyl, etc.), pyrrolidinyl, imidazolidinyl, piperidino, piperazinyl, etc.;

unsaturated condensed heterocyclic groups containing 1 through 4 nitrogen atoms as ring atoms, such as indolyl, isoindolyl, indolizinyl, benzimidazolyl, quinolyl, isoquinolyl, indazolyl, benzotriazolyl, etc.;

saturated condensed heterocyclic groups containing 1 through 4 nitrogen atoms, such as 7-azabicyclo[2.2.1]heptyl, 3-azabicyclo[3.2.2]nonanyl, etc.;

unsaturated 3- through 8-membered (preferably 5-or 6-membered) heteromonocyclic groups containing 1 or 2 oxygen atoms and 1 through 3 nitrogen atoms as ring atoms, such as oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3- through 8-membered (more preferably 5- or 6-membered) heteromonocyclic groups containing 1 or 2 oxygen atoms and 1 through 3 nitrogen atoms, such as morpholinyl, sydnonyl, etc.;

unsaturated condensed heterocyclic groups containing 1 or 2 oxygen atoms and 1 through 3 nitrogen atoms, such as benzoxazolyl, benzoxadiazolyl, etc.;

unsaturated 3- through 8-membered (more preferably 5- or 6-membered) heteromonocyclic groups containing 1 or 2 sulfur atoms and 1 through 3 nitrogen atoms, such as thiazolyl, isothiazolyl, thiadiazolyl (e.g. 1,2,3-thiadiazolyl, 1,2,4-thiadiazoyl, 1,3,4-thiadiazolyl, 1,2,5-thiadiazolyl, etc.), dihydrothiazinyl, etc.;

saturated 3- through 8-membered (more preferably 5- or 6-membered) heteromonocyclic groups containing 1 or 2 sulfur atoms and 1 through 3 nitrogen atoms, such as thiazolidinyl etc.; and unsaturated condensed heterocyclic groups containing 1 or 2 sulfur atoms and 1 through 3 nitrogen atoms, such as benzothiazolyl, benzothiadiazolyl, etc.

The preferred example, among the above various groups, may be saturated 3- through 8-membered heteromonocyclic groups containing 1 through 4 nitrogen atoms, saturated condensed heterocyclic groups containing 1 through 4 nitrogen atoms, and saturated 3- through 8-membered heteromonocyclic groups containing 1 or 2 oxygen atoms and 1 through 3 nitrogen atoms.

Those "nitrogen-containing heterocyclic groups" may have one or more suitable substituents such as said lower alkyl groups; hydroxy(lower)alkyl groups such as hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.; lower alkoxy(lower)alkyl groups such as methoxymethyl, 2-methoxyethyl, 1-ethoxyethyl, 3-propoxypropyl, 2-(tert-butoxy)butyl, 5-pentyloxypentyl, 3-hexyloxyhexyl, etc.; acyloxy(lower)alkyl groups such as lower alkanoyloxy(lower)alkyl groups (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc.); protected carboxy such as said lower alkoxycarbonyl groups; carboxy; and acyl(lower)alkyl groups such as alkanoyl(lower)alkyl groups (e.g. formylmethyl, 1-formylethyl, 2-acetylethyl, 2-formylpropyl, 3-propionylpropyl, 4-formylbutyl, 2-butyrylbutyl, 1-(formylmethyl)ethyl, 3-formylpentyl, 1-isobutyrylpentyl, 4-pivaloylpentyl, 2-formylhexyl, 6-hexanoylhexyl, etc.), carboxy(lower)alkyl groups (e.g. carboxymethyl, 1-carboxyethyl, 2-carboxypropyl, 1-(carboxymethyl)ethyl, 4-carboxybutyl, 3-carboxypentyl, 2-carboxyhexyl, etc.), and protected carboxy(lower)alkyl groups [preferably esterified carboxy(lower)alkyl groups, more preferably lower alkoxycarbonyl(lower)alkyl groups such as methoxycarbonylmethyl, 2-methoxycarbonylethyl, 1-ethoxycarbonylethyl, 2-propoxycarbonylpropyl, 1-(methoxycarbonylmethyl)ethyl, 4-t-butoxycarbonylbutyl, 3-pentyloxycarbonylpentyl, 2-hexyloxycarbonylhexyl, etc. and amidated carboxy(lower)alkyl groups, more preferably carbamoyl(lower)alkyl groups, N-(lower)alkylcarbamoyl (lower)alkyl groups such as N-ethylcarbamoylmethyl etc., N,N-di(lower)alkylcarbamoyl(lower)alkyl groups such as N,N-diethylcarbamoylmethyl, etc.], among others.

The preferred example of said "nitrogen-containing heterocyclic group which may have one or more suitable substituents" may include piperidino which may have 1 through 4 suitable substituents selected from among ($C_1$–$C_4$) alkyl, hydroxy($C_1$–$C_4$)alkyl, ($C_1$–$C_4$)alkoxy($C_1$–$C_4$)alkyl, ($C_1$–$C_4$)alkanoyloxy($C_1$–$C_4$)alkyl, ($C_1$–$C_4$)alkoxycarbonyl, carboxy, ($C_1$–$C_4$)alkanoyl($C_1$–$C_4$)alkyl, carboxy($C_1$–$C_4$) alkyl, ($C_1$–$C_4$)alkoxycarbonyl($C_1$–$C_4$)alkyl, carbamoyl ($C_1$–$C_4$)alkyl, N-($C_1$–$C_4$)alkylcarbamoyl($C_1$–$C_4$)alkyl and N,N-di($C_1$–$C_4$)alkylcarbamoyl($C_1$–$C_4$)alkyl, such as piperidino, 2-methylpiperidino, 2-ethylpiperidino, 3-ethylpiperidino, 4-ethylpiperidino, 2-propylpiperidino, 4-isopropylpiperidino, 2-butylpiperidino, 3-(tert-butyl) piperidino, 2,2,6,6-tetramethylpiperidino, 2,2-dimethyl-6,6-diethylpiperidino, 2-hydroxymethylpiperidino, 3-hydroxymethylpiperidino, 2-(1-hydroxyethyl)piperidino, 2-(2-hydroxyethyl)piperidino, 3-(2-hydroxyethyl) piperidino, 4-(2-hydroxyethyl)piperidino, 2-(3-hydroxypropyl)piperidino, 3-(2-hydroxybutyl)piperidino, 2-(1-methyl-1-hydroxymethylethyl)piperidino, 2-methoxymethylpiperidino, 2-(2-methoxyethyl)piperidino, 2-(1-ethoxyethyl)piperidino, 3-(3-propoxypropyl) piperidino, 4-{2-(tert-butoxy)butyl}piperidino, 2-acetoxymethylpiperidino, 3-(1-acetoxyethyl)piperidino, 2-(2-acetoxyethyl)piperidino, 3-(2-propionyloxyethyl) piperidino, 4-(3-propionyloxypropyl)piperidino, 2-(2-butyryloxybutyl)piperidino, 2-methoxycarbonylpiperidino, 2-ethoxycarbonylpiperidino, 2-propoxycarbonylpiperidino, 3-butoxycarbonylpiperidino, 4-(tert-butoxycarbonyl) piperidino, 2-carboxypiperidino, 3-carboxypiperidino, 4-carboxypiperidino, 2-(2-hydroxyethyl)-3-methylpiperidino, 2-(2-hydroxyethyl)-4-carboxypiperidino, 2-formylmethylpiperidino, 2-(1-formylethyl)piperidino, 3-(2-acetylethyl)piperidino, 4-(2-formylpropyl)piperidino, 2-(3-propionylpropyl)piperidino, 2-(4-formylbutyl)-piperidino, 3-(2-butyrylbutyl)piperidino, 2-[1-(formylmethyl)ethyl]piperidino, 2-carboxymethylpiperidino, 2-(1-carboxyethyl)piperidino, 3-(2-carboxypropyl)piperidino, 4-[1-(carboxymethyl)ethyl] piperidino, 2-(4-carboxybutyl)piperidino, 2-methoxycarbonylmethylpiperidino, 2-(2-methoxycarbonylethyl)piperidino, 3-(1-ethoxycarbonylethyl)piperidino, 4-(2-propoxycarbonylpropyl)piperidino, 2-[1-(methoxycarbonylmethyl)ethyl]piperidino, 2-(4-t-butoxycarbonylbutyl)piperidino, etc.;

Pyrrolidin-1-yl which may have ($C_1$–$C_4$)alkoxy-($C_1$–$C_4$) alkyl, such as pyrrolidin-1-yl, 2-methoxymethylpyrrolidin-1-yl, 2-(2-methoxyethyl) pyrrolidin-1-yl, 2-(1-ethoxyethyl)pyrrolidin-1-yl, 3-(3-propoxypropyl)pyrrolidin-1-yl, 3-{2 -(tert-butoxy) butyl}pyrrolidin-1-yl, etc.;

perhydroazepin-1-yl such as perhydro-1H-azepin-1-yl;

piperazin-1-yl which may have ($C_1$–$C_4$)alkyl, such as piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 2-butylpiperazin-1-yl, 3-(tert-butyl)piperazin-1-yl, etc.;

morpholino;

7-azabicyclo[2.2.1]heptan-7-yl; and 3-azabicyclo[3.2.2]nonan-3-yl, among others.

The most preferred example may be piperidino, 2-methylpiperidino, 2-ethylpiperidino, 3-ethylpiperidino, 4-ethylpiperidino, 2-propylpiperidino, 2,2,6,6-tetramethylpiperidino, 2-hydroxymethylpiperidino, 2-(2-hydroxyethyl)piperidino, 4-(2-hydroxyethyl)piperidino, 2-methoxymethylpiperidino, 2-(2-methoxyethyl)piperidino, 2-acetoxymethylpiperidino, 2-(2-acetoxyethyl)piperidino, 2-ethoxycarbonylpiperidino, 2-carboxypiperidino, 2-(methoxycarbonylmethyl)piperidino, 2-carboxymethylpiperidino, 2-carbamoylmethylpiperidino, 2-(N-ethylcarbamoylmethyl)piperidino, 2-N,N-diethylcarbamoylmethyl)piperidino, pyrrolidin-1-yl, 2-methoxymethylpyrrolidin-1-yl, perhydro-1H-azepin-1-yl, 4-methylpiperazin-1-yl, morpholino, 7-azabicyclo[2.2.1]heptan-7-yl, 3-azabicyclo[3.2.2]nonan-3-yl, etc.

Suitable "aryl group" may include phenyl, naphthyl, indenyl and anthryl, and said "aryl" may have one or more suitable substituents such as halogen (e.g. fluoro, chloro, bromo and iodo), lower alkoxy (e.g. methoxy, ethoxy, propoxy, tert-butoxy, pentyloxy and hexyloxy), nitro, amino, and said protected amino, among others.

The preferred example of said "aryl group which may have one or more suitable substituents" may include phenyl which may have 1 through 3 suitable substituents selected from among halogen, ($C_1$–$C_4$)alkoxy, nitro, amino, ($C_1$–$C_4$) alkanoylamino, ($C_1$–$C_4$) alkoxycarbonylamino, ($C_1$–$C_4$) alkanesulfonylamino, ($C_1$–$C_4$)alkylamino and di($C_1$–$C_4$) alkylamino. The more preferred one, among them, may be phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino and phenyl having dimethylamino.

Suitable "heterocyclic group" may include the groups mentioned for said "nitrogen-containing heterocyclic group";

unsaturated 3- through 8-membered (more preferably 5- or 6-membered) heteromonocyclic groups containing one oxygen atom, such as furyl etc.;

unsaturated 3- through 8-membered (more preferably 5- or 6-membered) heteromonocyclic groups containing 1 oxygen atom and 1 or 2 sulfur atoms, such as dihydrooxathiynyl etc.;

unsaturated condensed heterocyclic groups containing 1 or 2 sulfur atoms, such as benzothienyl, benzodithiinyl, etc.; and unsaturated condensed heterocyclic groups containing one oxygen atom and 1 or 2 sulfur atoms, such as benzoxathiynyl, among others. The preferred examples, among them, are unsaturated 3- through 8-membered heteromonocyclic groups containing 1 through 4 nitrogen atoms and the more preferred examples are pyridyl groups. The most preferred example is 2-pyridyl, 3-pyridyl or 4-pyridyl.

Suitable "lower alkenyl having halogen" may include 1-fluorovinyl, 1-bromovinyl, 1-chloro-2-methylvinyl, 1-bromo-1-propenyl, 2-chloro-2-propenyl, 1-iodo-1-butenyl, 1-bromo-2-methyl-1-propenyl, 3-bromo-1,3-butadienyl, 1-chloro-1-pentenyl, 4-chloro-4-pentenyl, 1-bromo-1-hexenyl, etc.

Suitable "lower alkoxy" may include methoxy, ethoxy, propoxy, isopropoxy, butoxy, tert-butoxy, pentyloxy, hexyloxy, etc Suitable "halogen" may include fluoro, chloro, bromo and iodo.

Suitable "leaving group" may include di(lower) alkylamino groups such as dimethylamino, diethylamino, N-ethylpropylamino, dibutylamino, N-pentylhexylamino, etc. , said lower alkoxy, said halogen, and lower alkylthio such as methylthio, ethylthio, propylthio, butylthio, pentylthio, hexylthio, etc.

Suitable "unsaturated heterocyclic group" of said "unsaturated heterocyclic group optionally having one or more suitable substituents" may include unsaturated monocyclic or polycyclic heterocyclic groups containing at least one hetero atom such as nitrogen, oxygen, sulfur, etc.

Suitable example of this "unsaturated heterocyclic group" may include unsaturated 3- through 8-membered (more preferably 5-~7-membered) heteromonocyclic groups containing 1 through 4 nitrogen atoms, such as azepinyl (e.g. 1H-azepinyl etc.), pyrrolyl, pyrrolinyl, imidazolyl, pyrazolyl, pyridyl, dihydropyridyl (e.g. 1,2-dihydropyridyl, 1,4-dihydropyridyl, etc.), tetrahydropyridyl (e.g. 1,2,3,6-tetrahydropyridyl etc.), pyrimidinyl, dihydropyrimidinyl (e.g. 1,2-dihydropyrimidinyl, etc.), pyrazinyl, pyridazinyl, dihydropyridazinyl (e.g. 2,3-dihydropyridazinyl, 1,4-dihydropyridazinyl, etc.), tetrahydropyridazinyl (e.g. 2,3,4,5-tetrahydropyridazinyl, etc.), triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

unsaturated condensed heterocyclic groups containing 1 through 4 nitrogen atoms, such as indolyl, isoindolyl, indolizinyl, benzimidazolyl, quinolyl, dihydroquinolyl (e.g. 2,3-dihydroquinolyl, etc.), isoquinolyl, indazolyl, benzotriazolyl, etc.;

unsaturated 3- through 8-membered (more preferably 5- or 6-membered) heteromonocyclic groups containing 1 or 2 oxygen atoms and 1 through 3 nitrogen atoms, such as oxazolyl, isoxazolyl, dihydroisoxazolyl (e.g. 2,5-dihydroisoxazolyl), oxadiazolyl (e.g. 1,2,4-oxadiazolyl, 1,3,4-oxadiazolyl, 1,2,5-oxadiazolyl, etc.), etc.;

unsaturated condensed heterocyclic groups containing 1 or 2 oxygen atoms and 1 through 3 nitrogen atoms, such as benzoxazolyl, benzoxadiazolyl, etc.;

unsaturated 3- through 8-membered (more preferably 5- or 6-membered) heteromonocyclic groups containing 1 or 2 sulfur atoms and 1 through 3 nitrogen atoms, such as thiazolyl, dihydrothiazolyl (e.g. 2,3-dihydrothiazolyl, etc.), isothiazolyl, thiadiazolyl (e g. 1,2,3-thiadiazolyl, 1,2,4-thiadiazolyl, 1,3,4-thiadiazolyl, 1,2,5-thiadiazolyl, etc.), dihydrothiazinyl, etc.;

unsaturated condensed heterocyclic groups containing 1 or 2 sulfur atoms and 1 through 3 nitrogen atoms, such as benzothiazolyl, benzothiadiazolyl (e.g. benzo[d][1,2,3]thiadiazolyl, etc.) and imidazothiadiazolyl (e.g. 5H-imidazo[2,1-9 [1,3,4]-thiadiazolyl, etc.), etc.;

unsaturated 3- through 8-membered (more preferably 5- or 6-membered) heteromonocyclic groups containing 1 or 2 sulfur atoms, such as thienyl, dihydrothiinyl, etc.;

unsaturated 3- through 8-membered (more preferably 5- or 6-membered) heteromonocyclic groups containing one oxygen atom, such as furyl etc.;

unsaturated 3- through 8-membered (more preferably 5- or 6-membered) heteromonocyclic groups containing one oxygen atom and 1 or 2 sulfur atoms, such as dihydrooxathiinyl etc.;

unsaturated condensed heterocyclic groups containing 1 or 2 sulfur atoms, such as benzothienyl, benzodithiinyl, etc.; and unsaturated condensed heterocyclic groups containing 1 oxygen atom and 1 or 2 sulfur atoms, such as benzoxathiinyl etc.

The preferred example, among them, may be unsaturated heterocyclic groups containing at least one nitrogen atom as hetero atom and the more preferred one may be unsaturated 3- through 8-membered heteromonocyclic groups containing 1 through 4 nitrogen atoms and unsaturated condensed heterocyclic groups containing 1 or 2 sulfur atoms and 1 through 3 nitrogen atoms. The still more preferred one may be pyridazinyl, dihydropyridazinyl, tetrahydropyridazinyl, pyrimidinyl, dihydropyrimidinyl, pyridyl, dihydropyridyl, tetrahydropyridyl, pyrazolyl, imidazothiadiazolyl, etc. and the most preferred examples are pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahydropyridyl, pyrazolyl and imidazo[2,1-b][1,3,4]thiadiazolyl.

The "unsaturated heterocyclic group" mentioned above may have one or more (preferably 1 through 4) suitable substituents, such as lower alkyl groups (e.g. methyl, ethyl, propyl, isopropyl, butyl, tert-butyl, pentyl, hexyl, etc.) which may have one or more (preferably 1 through 4) suitable substituents such as those mentioned hereinafter; carboxy (lower)alkenyl groups such as 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc.; amino; di(lower)alkylamino such as dimethylamino, N-methylethylamino, dipropylamino, N-butyl-(2-methylbutyl)amino, N-pentylhexylamino, etc.; halogen such as fluoro, chloro, bromo and iodo; lower alkoxy such as methoxy, ethoxy, propoxy, isopropoxy, butoxy, tert-butoxy, pentyloxy, hexyloxy, etc.; oxo; hydroxy; cyano; and the undermentioned acyl groups.

Suitable "acyl group" may include lower alkanoyl groups (e.g. formyl, acetyl, propionyl, butyryl, isobutyryl, pivaloyl, hexanoyl, etc.), carboxy, protected carboxy, etc.

Suitable example of "protected carboxy" may include esterified carboxy, preferred examples of which are lower alkoxycarbonyl groups (e.g. methoxycarbonyl, ethoxycarbonyl, propoxycarbonyl, tert-butoxycarbonyl, pentyloxycarbonyl, hexyloxycarbonyl, etc.), etc. and amidated carboxy, preferred examples of which are carbamoyl, N,N-di(lower)alkylcarbamoyl the two lower alkyl groups of which may jointly form a 3- through 6-membered ring (e.g. N,N-dimethylcarbamoyl, N-methyl-N-ethylcarbamoyl, N,N-diethylcarbamoyl, N,N-dipropylcarbamoyl, N-butyl-N-tert-butylcarbamoyl, N,N-dipentylcarbamoyl, N-pentyl-N-hexylcarbamoyl, 1-aziridinylcarbonyl, 1-azetidinylcarbonyl, 1-pyrrolidinylcarbonyl, piperidinocarbonyl, etc.), etc.

Suitable example of "suitable substituents" for said "lower alkyl groups which may have one or more suitable substituents" may include hydroxy, said halogen, said lower alkoxy, said acyl, etc.

Suitable example of the "lower alkyl group having one or more suitable substituents" may include lower alkyl groups having hydroxy and halogen, such as 1-hydroxy-1-chloromethyl, 1-hydroxy-2-chloroethyl, 2-hydroxy-3-fluoropropyl, 2-hydroxy-3,3,3-trichloropropyl, 3-bromo-4-hydroxy-4-iodobutyl, 1-chloro-2-hydroxy-4-fluoropentyl, 3,4-dihydroxy-6-chlorohexyl, etc.;

hydroxy(lower)alkyl groups such as hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl, etc.;

lower alkoxy(lower)alkyl groups such as methoxymethyl, ethoxymethyl, 2-ethoxyethyl, 1-propoxyethyl, 3-isopropoxypropyl, 2-butoxybutyl, 1-tert-butoxymethyl-1-methylethyl, 5-pentyloxypentyl, hexyloxymethyl, 3-hexyloxyhexyl, etc.;

acyl(lower)alkyl groups, in which the preferred example may be carboxy(lower)alkyl groups (e.g. carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl, 2-carboxyhexyl, etc.) and protected carboxy(lower)alkyl groups, preferably esterified carboxy(lower)alkyl groups and amidated carboxy (lower)alkyl groups, such as lower alkoxycarbonyl (lower)alkyl groups (e.g. methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-tert-butoxycarbonylmethyl-1-methylethyl, 5-pentyloxycarbonylpentyl, hexyloxycarbonylmethyl, 3-hexyloxycarbonylhexyl, etc.), carbamoyl(lower)alkyl groups (e.g. carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc.), and N,N-di(lower)alkylcarbamoyl(lower)alkyl groups, the two lower alkyl groups on the nitrogen atom thereof optionally forming a 3- through 6-membered ring between them [e.g. N,N-dimethylcarbamoylmethyl, 2-(N,N-dimethylcarbamoyl)ethyl, 2-(N-methyl-N-ethylcarbamoyl)ethyl, 3-(N-methyl-N-ethylcarbamoyl)propyl, 2-(N,N-dipropylcarbamoyl)-1-methylethyl, 4-(N,N-dipropylcarbamoyl)butyl, 1-(N,N-dimethylcarbamoyl)methyl-1-methylethyl, 5-(N-pentyl-N-hexylcarbamoyl)pentyl, 3-(N-pentyl-N-hexylcarbamoyl)hexyl, (1-aziridinylcarbonyl)methyl, 2-(1-azetidinylcarbonyl)ethyl, 2-(piperidinocarbonyl) ethyl, 3-(1-pyrrolidinylcarbonyl)propyl, 2-(piperidinocarbonyl)-1-methylethyl, 4-(1-azetidinylcarbonyl)butyl, 1-(1-aziridinylcarbonyl) methyl-1-methylethyl, 3-(1-pyrrolidinylcarbonyl) pentyl, 6-(piperidinocarbonyl)hexyl, etc. ], etc.

The preferred substituent on said "unsaturated heterocyclic group" may include lower alkyl, lower alkyl having hydroxy and halogen, hydroxy(lower)alkyl, lower alkoxy (lower)alkyl, carboxy(lower)alkyl, lower alkoxycarbonyl (lower)alkyl, carbamoyl(lower)alkyl, N,N-di(lower) alkylcarbamoyl(lower)alkyl, the two lower alkyl groups on its nitrogen atom optionally forming a 3- through 6-membered ring between them, carboxy(lower)alkenyl, di(lower)alkylamino, halogen, lower alkoxy, oxo, carboxy, lower alkoxycarbonyl, lower alkanoyl, amino, cyano and hydroxy. The more preferred one, among them, maybe $(C_1-C_4)$alkyl, $(C_1-C_4)$alkyl having hydroxy and halogen, hydroxy$(C_1-C_4)$alkyl, $(C_1-C_4)$alkoxy$(C_1-C_4)$alkyl, carboxy$(C_1-C_4)$alkyl, $(C_1-C_4)$alkoxycarbonyl$(C_1-C_4)$alkyl, carbamoyl$(C_1-C_4)$alkyl, N,N-di$(C_1-C_4)$alkylcarbamoyl $(C_1-C_4)$alkyl, piperidinocarbonyl$(C_1-C_4)$alkyl, carboxy $(C_2-C_4)$alkenyl, di$(C_1-C_4)$alkylamino, halogen, $(C_1-C_4)$ alkoxy, oxo, carboxy, $(C_1-C_4)$alkoxycarbonyl, $(C_1-C_4)$ alkanoyl, amino, cyano and hydroxy. The most preferred one may be methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano and hydroxy.

The "unsaturated heterocyclic group" of said "unsaturated heterocyclic group which may have one or more suitable substituents" may have one or more (preferably 1 through 4) substituents such as those mentioned below in addition to the substituents already mentioned.

The substituents mentioned above may include amino (lower)alkyl; lower alkylamino(lower)alkyl; carboxy(lower) alkylamino(lower)alkyl; protected carboxy(lower) alkylamino(lower)alkyl; lower alkylamino(lower)alkyl having hydroxy and aryloxy; protected amino(lower)alkyl; cyano(lower)alkyl; cyano(higher)alkyl; lower alkyl having heterocyclic group which may have one or more suitable substituents; higher alkyl having heterocyclic group which may have one or more suitable substituents; ar(lower)alkyl; lower alkenyl, heterocyclic groups which may have one or more suitable substituents; cyclo(lower)alkyl which may have one or more suitable substituents; or cyclo(lower) alkenyl which may have one or more suitable substituents.

The above substituent groups are now explained in detail.

Suitable "amino(lower)alkyl" may include aminomethyl, 1-aminoethyl, 2-aminoethyl, 2-aminopropyl, 3-aminobutyl, 2-amino-1,1-dimethylethyl, 5-aminopentyl, 1-aminohexyl, etc. The preferred example, among them, may be amino $(C_1-C_4)$alkyl and the still more preferred is 2-aminoethyl.

Suitable "lower alkylamino(lower)alkyl" may include mono or di(lower)alkylamino(lower)alkyl groups such as methylaminomethyl, 2-(ethylamino)ethyl, 3-(propylamino) propyl, 2-(propylamino)butyl, 2-(t-butylamino)-1,1-dimethylethyl, 4-pentylaminopentyl, 6-hexylaminohexyl, dimethylaminomethyl, 2-dimethylaminoethyl, 1-(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl, etc. The preferred example, among them, may be di(lower)alkylamino(lower)alkyl groups, the more preferred one may be di$(C_1-C_4)$alkylamino $(C_1-C_4)$alkyl groups, and the most preferred one may be 2-dimethylaminoethyl, 3-dimethylaminopropyl and 4-dimethylaminobutyl.

Suitable "carboxy(lower)alkylamino(lower)alkyl" may include carboxymethylaminomethyl, 2-(carboxymethylamino)ethyl, 2-(1-carboxyethylamino) ethyl, 3-(2-carboxypropylamino)propyl, 2-(3-carboxypropylamino)butyl, 2-(2-carboxy-1,1-dimethylethylamino)-1,1-dimethylethyl, 4-(5-carboxypentylamino)pentyl, 6-(3-carboxyhexylamino) hexyl, etc. The more preferred example, among them, may be carboxy$(C_1-C_4)$alkylamino$(C_1-C_4)$alkyl groups and the most preferred one may be 2-(carboxymethylamino)ethyl.

Suitable "protected carboxy" of said "protected carboxy (lower)alkylamino(lower)alkyl" may include esterified carboxy, and as examples of the ester moiety in said esterified carboxy group, there may be mentioned lower alkyl esters (e.g. methyl ester, ethyl ester, propyl ester, isopropyl ester, butyl ester, isobutyl ester, t-butyl ester, pentyl ester, hexyl ester, 1-cyclopropylethyl ester, etc.) which may have suitable substituents, thus including, among others, lower alkanoyloxy(lower)alkyl esters (e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.), lower alkanesulfonyl(lower)alkyl esters (e.g. 2-mesylethyl ester etc.) or mono- (or di- or tri-)halo(lower)alkyl esters (e.g. 2-iodoethyl ester, 2,2,2-trichloroethyl ester, etc.); lower alkenyl esters (e.g. vinyl ester, allyl ester, etc.); lower alkinyl esters (e.g. ethinyl ester, propinyl ester, etc.); ar(lower)alkyl esters which may have suitable substituents [e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-t-butylbenzyl ester, etc.]; aryl esters which may have suitable substituents (e.g. phenyl ester, 4-chlorophenyl ester, tolyl ester, 4-t-butylphenyl ester, xylyl ester, mesityl ester, cumenyl ester, etc.), etc.

Suitable "protected carboxy(lower)alkylamino(lower) alkyl" may include esterified carboxy(lower)alkylamino (lower)alkyl groups. The preferred example, among them, may be lower alkoxycarbonyl(lower)alkylamino(lower) alkyl groups, such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl, etc. The more preferred one may be $(C_1-C_4)$alkoxycarbonyl$(C_1-C_4)$ alkylamino $(C_1-C_4)$alkyl groups and the most preferred one may be 2-(ethoxycarbonylmethylamino)ethyl.

Suitable "lower alkylamino(lower)alkyl having hydroxy and aryloxy" may include said "lower alkylamino(lower) alkyl" having both "hydroxy" and "aryloxy" (e.g. phenoxy, tolyloxy, naphthyloxy, etc.), and the suitable example may be 1-(1-naphthyloxy)-1-hydroxymethylaminomethyl, 2-(1-hydroxy-2-phenoxyethylamino)ethyl, 2-[2-hydroxy-3-(1-naphthyloxy)propylamino]ethyl, 2-[4-hydroxy-3-(p-tolyloxy)butylamino]propyl, 2-[4-hydroxy-1-(2-naphthyloxy)butylamino]-1,1-dimethylethyl, 4-[1-hydroxy-5-(1-naphthyloxy)pentylamino]pentyl and 6-[2-hydroxy-4-(2-naphthyloxy)hexylamino]hexyl. The preferred one, among them, may be $(C_1-C_4)$alkylamino $(C_1-C_4)$alkyl groups having hydroxy and naphthyloxy, and the more preferred one may be 2-[2-hydroxy-3-(1-naphthyloxy) propylamino]ethyl.

Suitable "protected amino(lower)alkyl" may include acylamino(lower)alkyl groups.

The suitable example of "acylamino" may be lower alkanoylamino (e.g. formylamino, acetylamino, propionylamino, hexanoylamino, pivaloylamino, etc.), mono-(or di- or tri-)halo(lower)alkanoylamino (e.g. chloroacetylamino, trifluoroacetylamino, etc.), lower alkoxycarbonylamino (e.g. methoxycarbonylamino, ethoxycarbonylamino, t-butoxycarbonylamino, t-pentyloxycarbonylamino, hexyloxycarbonylamino, etc.), mono-(or di- or tri-)halo(lower)alkoxycarbonylamino (e.g. chloromethoxycarbonylamino, dichloroethoxycarbonylamino, trichloroethoxycarbonylamino, etc.), aroylamino (e.g. benzoylamino, toluoylamino, xyloylamino, naphthoylamino, etc.), ar(lower)alkanoylamino, for example phenyl(lower)alkanoylamino (e.g. phenylacetylamino, phenylpropionylamino, etc.), aryloxycarbonylamino (e.g. phenoxycarbonylamino, naphthyloxycarbonylamino, etc.), aryloxy(lower) alkanoylamino, for example phenoxy(lower)alkanoylamino (e.g. phenoxyacetylamino, phenoxypropionylamino, etc.), arylglyoxyloylamino (e.g. phenylglyoxyloylamino, naphthylglyoxyloylamino, etc.), ar(lower) alkoxycarbonylamino which may have suitable substituents, for example phenyl(lower)alkoxycarbonylamino which may have nitro or lower alkoxy (e.g. benzyloxycarbonylamino, phenethyloxycarbonylamino, p-nitrobenzyloxycarbonylamino, p-methoxybenzyloxycarbonylamino, etc.), thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino (e.g. methylsulfonylamino, ethylsulfonylamino, propylsulfonylamino, isopropylsulfonylamino, pentylsulfonylamino, butylsulfonylamino, etc.), arylsulfonylamino (e.g. phenylsulfonylamino, tolylsulfonylamino, xylylsulfonylamino, naphthylsulfonylamino, etc.), ar(lower) alkylsulfonylamino, for example phenyl(lower) alkylsulfonylamino (e.g. benzylsulfonylamino, phenethylsulfonylamino, benzhydrylsulfonylamino, etc.), imides (e.g. 1,2-cyclohexanedicarboximide, succinimide, phthalimide, etc.), etc.

The preferred example of said "protected amino(lower)alkyl" may include imido(lower)alkyl such as phthalimidomethyl, 2-phthalimidoethyl, 1-(1,2-cyclohexanedicarboximido)ethyl, 2-succinimidopropyl, 3-phthalimidobutyl, 2-(1,2-cyclohexanedicarboximide)-1,1-dimethylethyl, 5-phthalimidopentyl and 1-phthalimidohexyl, etc. The more preferred one may be imido($C_1$–$C_4$)alkyl and the most preferred one may be 2-phthalimidoethyl.

Suitable "cyano(lower)alkyl" may include cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl and 6-cyanohexyl, etc. The preferred example, among them, may be cyano($C_1$–$C_6$)alkyl groups and the most preferred one may be cyanomethyl, 2-cyanoethyl, 3-cyanopropyl, 4-cyanobutyl, 5-cyanopentyl and 6-cyanohexyl.

Suitable "cyano(higher)alkyl" may include 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoeicosyl, etc. The preferred example, among them, may be cyano ($C_7$–$C_{16}$)alkyl groups and the more preferred one may be 7-cyanoheptyl, 8-cyanooctyl, 9-cyanononyl, 10-cyanodecyl and 12-cyanododecyl.

Suitable "lower alkyl" may include straight-chain or branched-chain alkyl groups such as methyl, ethyl, propyl, isopropyl, butyl, t-butyl, pentyl, hexyl, etc.

Suitable "lower alkenyl" may include straight-chain or branched-chain alkenyl groups such as vinyl, allyl, 2-butenyl, 2-methyl-2-propenyl, 4-pentenyl, 3-hexenyl, etc. The preferred example, among them, may be ($C_2$–$C_4$) alkenyl groups and the more preferred one may be vinyl.

Suitable "lower alkyl" of said "lower alkyl having a heterocyclic group which may have one or more suitable substituents" may include the same lower alkyl groups as mentioned above. The preferred example may be ($C_1$–$C_6$) alkyl and the most preferred one may be methyl, ethyl, propyl, butyl, pentyl and hexyl.

Suitable "higher alkyl" of said "higher alkyl having a heterocyclic group which may have one or more suitable substituents" may include heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl, 12-ethylheptadecyl, icosyl, etc. The preferred example, among them, may be ($C_7$–$C_{16}$)alkyl groups and the more preferred one may be heptyl, octyl, nonyl, decyl and dodecyl.

Referring, to "lower alkyl having a heterocyclic group which may have one or more suitable substituents" and "higher alkyl having a heterocyclic group which may have one or more suitable substituents", suitable "heterocyclic group" may be saturated or unsaturated monocyclic or polycyclic heterocyclic groups containing at least one hetero atom selected from among oxygen, sulfur and nitrogen. The particularly preferred example of said heterocyclic group may include unsaturated 3- through 8-membered heteromonocyclic groups containing 1 through 4 nitrogen atoms, such as pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), etc.;

3- through 8-membered saturated heteromonocyclic groups containing 1 through 4 nitrogen atoms, such as pyrrolidinyl, imidazolidinyl, piperidyl (e.g. piperidino, etc.), piperazinyl, etc.;

unsaturated fused heterocyclic groups containing 1 through 5 nitrogen atoms, such as indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl etc.), dihydrotriazolopyridazinyl, etc.;

3- through 8-membered unsaturated heteromonocyclic groups containing 1 or 2 oxygen atoms and 1 through 3 nitrogen atoms, such as oxazolyl, isoxazolyl, oxadiazolyl (e.g. 1,2,4-oxadiazolyl, 1,3,4-oxadiazolyl, 1,2,5-oxadiazolyl, etc.), etc.;

3- through 8-membered saturated heteromonocyclic groups containing 1 or 2 oxygen atoms and 1 through 3 nitrogen atoms, such as morpholinyl, oxazolidinyl (e.g. 1,3-oxazolidinyl etc.), etc.;

unsaturated condensed heterocyclic groups containing 1 or 2 oxygen atoms and 1 through 3 nitrogen atoms, such as benzoxazolyl, benzoxadiazolyl, etc.;

3- through 8-membered unsaturated heteromonocyclic groups containing 1 or 2 sulfur atoms and 1 through 3 nitrogen atoms, such as 1,3-thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl), etc.;

3- through 8-membered saturated heteromonocyclic groups containing 1 or 2 sulfur atoms and 1 through 3 nitrogen atoms, such as thiazolidinyl etc.;

3- through 8-membered unsaturated heteromonocyclic groups containing 1 sulfur atom, such as thienyl etc.;

unsaturated condensed heterocyclic groups containing 1 or 2 sulfur atoms and 1 through 3 nitrogen atoms, such as benzothiazolyl, benzothiadiazolyl, etc.;

3- through 8-membered unsaturated heteromonocyclic groups containing 1 or 2 oxygen atoms, such as furyl, pyranyl, dioxolyl, etc.;

3- through 8-membered saturated heteromonocyclic groups containing 1 or 2 oxygen atoms, such as oxolanyl, tetrahydropyranyl (e.g. tetrahydro-2H-pyran-2-yl etc.), dioxolanyl, etc.; and unsaturated condensed heterocyclic groups containing 1 or 2 oxygen atoms, such as isobenzofuranyl, chromenyl (e.g. 2H-chromen-3-yl etc.), dihydrochromenyl (e.g. 3,4-dihydro-2H-chromen-4-yl etc .), etc.

The preferred example of the above "heterocyclic group" may be 3- through 8-membered unsaturated heteromonocyclic groups containing 1 through 4 nitrogen atoms; 3- through 8-membered saturated heteromonocyclic groups containing 1 through 4 nitrogen atoms; 3- through 8-membered saturated heteromonocyclic groups containing 1 or 2 oxygen atoms and 1 through 3 nitrogen atoms; and 3- through 8-membered saturated heteromonocyclic groups containing 1 or 2 oxygen atoms. The preferred example, among them, may be pyridyl, tetrazolyl, piperidyl, piperazinyl, morpholinyl, oxazolidinyl and tetrahydropyranyl, and the more preferred one may be 4-pyridyl, 1H-tetrazol-5-yl, piperidino, 1-piperazinyl, morpholino, 1,3-oxazolidin-5-yl and tetrahydro-2H-pyran-2-yl.

The "heterocyclic group" mentioned above may have one or more (preferably 1 through 3) suitable substituents [for example, hydroxy(lower)alkyl groups (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc.), aryl groups which may have lower alkoxy (e.g. phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t-butoxyphenyl, 4-pentyloxyphenyl, 2-hexyloxyphenyl, etc.), oxo, etc.]. The preferred example, among said "suitable substituents", may be hydroxy($C_1$–$C_4$)alkyl, phenyl having ($C_1$–$C_4$)alkoxy, and oxo, and the more preferred one may be 2-hydroxyethyl, 2-methoxyphenyl and oxo.

Suitable "heterocyclic group" of said "heterocyclic group which may have one or more suitable substituents" may include the groups mentioned for the "heterocyclic group" of said "lower alkyl having a heterocyclic group which may have one or more suitable substituents" and of said "higher alkyl having a heterocyclic group which may have one or more suitable substituents". The preferred example may be unsaturated condensed heterocyclic groups containing 1 or 2 oxygen atoms, the more preferred one may be dihydrochromenyl groups, and the most preferred one may be 3,4-dihydro-2H-chromen-4-yl.

This "heterocyclic group" may have one or more (preferably 1 through 4) suitable substituents [for example, said lower alkyl, hydroxy, cyano, etc., more preferably ($C_1$–$C_4$)alkyl, hydroxy and cyano, the most preferably methyl, hydroxy and cyano].

Suitable "ar(lower)alkyl" may include mono-, di- or triphenyl(lower)alkyl groups (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc.), etc. The preferred example, among them, may be phenyl($C_1$–$C_4$) alkyl groups and the most preferred one may be benzyl.

As the suitable "nitrogen-containing heterocyclic group" of said "nitrogen-containing heterocyclic group which may have one or more suitable substituents", there can be mentioned the heterocyclic groups containing at least one nitrogen atom as a ring atom which are among the "heterocyclic groups" mentioned above, and this "nitrogen-containing heterocyclic group" may have one or more (preferably 1 through 3) suitable substituents (for example said hydroxy (lower)alkyl groups, said aryl groups which may have lower alkoxy, oxo, etc.).

Suitable "tetrazolyl(lower)alkyl" may include 1H-tetrazol-5-ylmethyl, 2-(1H-tetrazol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(1H-tetrazol-1-yl)pentyl, 5-(1H-tetrazol-5-yl)pentyl, 6-(1H-tetrazol-5-yl)hexyl, etc. The preferred example, among them, may be tetrazolyl ($C_1$–$C_6$)alkyl groups, and the more preferred one may be (1H-tetrazol-5-yl)methyl, 2-(1H-tetrazol-5-yl)ethyl, 3-(1H-tetrazol-5-yl)propyl, 4-(1H-tetrazol-5-yl)butyl, 5-(1H-tetrazol-5-yl)pentyl and 6-(1H-tetrazol-5-yl)hexyl.

Suitable "tetrazolyl(higher)alkyl" may include 7-(1H-tetrazol-5-yl)heptyl, 8-(1H-tetrazol-5-yl)octyl, 4-(1H-tetrazol-1-yl)octyl, 8-(1H-tetrazol-5-yl)-3-methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl)undecyl, 12-(1H-tetrazol-5-yl)dodecyl, 11-(1H-tetrazol-5-yl)-4-methylundecyl, 13-(1H-tetrazol-5-yl)tridecyl, 6-(1H-tetrazol-5-yl)tetradecyl, 15-(1H-tetrazol-5-yl)pentadecyl, 12-(1H-tetrazol-5-yl)hexadecyl, 17-(1H-tetrazol-1-yl) heptadecyl, 4-(1H-tetrazol-5-yl)octadecyl, 19-(1H-tetrazol-5-yl)nonadecyl, 1-(1H-tetrazol-1-yl)-12-ethylheptadecyl, 20-(1H-tetrazol-5-yl)eicosyl, etc. The preferred example, among them, may be tetrazolyl($C_7$–$C_{16}$)alkyl groups, and the more preferred one may be 7-(1H-tetrazol-5-yl)heptyl, 8-(1H-tetrazol-5-yl)octyl, 9-(1H-tetrazol-5-yl)nonyl, 10-(1H-tetrazol-5-yl)decyl and 12-(1H-tetrazol-5-yl)dodecyl.

Suitable "cyclo(lower)alkyl" may include cyclo($C_3$–$C_8$) alkyl groups such as cyclopropyl, cyclobutyl, cyclopentyl, cyclohexyl, cycloheptyl, cyclooctyl, etc. The preferred example, among them, may be cyclo($C_5$–$C_7$)alkyl groups such as cyclopentyl, cyclohexyl, cycloheptyl, etc.

The "cyclo(lower)alkyl" mentioned above may have one or more (preferably 1~3) suitable substituents selected from among, for example, acyl(lower)alkyl, acyl(lower) alkylidene, etc.

Suitable "cyclo(lower)alkenyl" may cyclo($C_3$–$C_8$)alkenyl groups such as cyclopropenyl, cyclobutenyl, cyclopentenyl, cyclohexenyl, cycloheptenyl, cyclooctenyl, etc. The preferred example, among them, may be cyclo($C_5$–$C_7$)alkenyl groups such as cyclopentenyl, cyclohexenyl, cycloheptenyl, etc., and the more preferred one may be cyclohexenyl or cycloheptenyl.

This "cyclo(lower)alkenyl" may have one or more (preferably 1~3) suitable substituents such as those mentioned above for "cyclo(lower)alkyl".

Suitable "acyl(lower)alkyl" may include carboxy(lower) alkyl groups such as carboxymethyl, 2-carboxyethyl, 3-carboxypropyl, 1-carboxymethylethyl, 4-carboxybutyl, 2-carboxymethyl-2-methylethyl, 5-carboxypentyl, 3-carboxyhexyl, etc. and lower alkanoyl(lower)alkyl groups such as acetylmethyl, formylmethyl, 2-acetyletyl, 2-propionylpropyl, 4-butyrylbutyl, 3-pentanoylpentyl, 6-hexanoylhexyl, etc. The preferred example, among them, may be carboxy($C_1$–$C_4$)alkyl or ($C_1$–$C_4$)alkanoyl($C_1$–$C_4$) alkyl, and the more preferred one may be carboxymethyl, 2-carboxyethyl, 3-carboxypropyl or acetylmethyl.

As other suitable example of said "acyl(lower)alkyl", there may be mentioned protected carboxy(lower)alkyl groups. The preferred example, among them, may be esterified carboxy(lower)alkyl groups. The more preferred one may be lower alkoxycarbonyl(lower)alkyl groups such as methoxycarbonylmethyl, ethoxycarbonylmethyl, 2-ethoxycarbonylethyl, 1-propoxycarbonylpropyl, 2-isopropoxycarbonylpropyl, butoxycarbonylmethyl, t-butoxycarbonylmethyl, 4-isobutoxycarbonylbutyl, 3-pentyloxycarbonylpentyl, 6-hexyloxycarbonylhexyl, (1-cyclopropylethoxycarbonyl)methyl, etc. and phenyl (lower)alkoxycarbonyl(lower)alkyl groups such as benzyloxycarbonylmethyl, 2-benzyloxycarbonylethyl, 1-phenethyloxycarbonylethyl, 3-benzyloxycarbonylpropyl, 2-benzyloxycarbonylbutyl, 2-phenethyloxycarbonylmethyl- 2-methylethyl, 3-benzyloxycarbonylpentyl, 6-benzyloxycarbonylhexyl, etc. The more preferred one may be ($C_1$–$C_4$)alkoxycarbonyl($C_1$–$C_4$)alkyl or phenyl($C_1$–$C_4$) alkoxycarbonyl($C_1$–$C_4$)alkyl groups and the particularly preferred one may be methoxycarbonylmethyl, ethoxycarbonylmethyl, t-butoxycarbonylmethyl, 2-benzyloxycarbonylethyl, and 3-benzyloxycarbonylpropyl.

Suitable example of "acyl(lower)alkylidene" may include carboxy(lower)alkylidene groups such as carboxymethylene, 2-carboxyethylidene, 2-carboxypropylidene, 4-carboxybutylidene, 5-carboxypentylidene, 3-carboxyhexylidene, etc. The preferred example, among them, may be carboxy($C_1$–$C_4$) alkylidene groups and the more preferred one may be carboxymethylene.

As other suitable example of "acyl(lower)alkylidene", there may be mentioned protected carboxy(lower)alkylidene groups. The preferred example, among them, may be esterified carboxy(lower)alkylidene groups. The more preferred one may be lower alkoxycarbonyl(lower)alkylidene groups such as methoxycarbonylmethylene, ethoxycarbonylmethylene, 2-ethoxycarbonylethylidene, 1-propoxycarbonylpropylidene, 2-isopropoxycarbonylpropylidene, butoxycarbonylmethylene, t-butoxycarbonylmethylene, 4-isobutoxycarbonylbutylidene, 3-pentyloxycarbonylpentylidene, 6-hexyloxycarbonylhexylidene, (1-cyclopropylethoxycarbonyl)methylene, etc. The further more preferred one may be ($C_1$–$C_4$)alkoxycarbonyl($C_1$–$C_4$) alkylidene groups, and the particularly preferred one may be methoxycarbonylmethylene, ethoxycarbonylmethylene and t-butoxycarbonylmethylene.

Referring to the pyrazolopyridine compound (I) described above, the specific compounds which are particularly preferred for the purposes of this invention are as follows.

(1) (2R)-1-[3-(2-Phenylpyrazolo[1,5-a]pyridin-3-yl) acryloyl]-2-(2-hydroxyethyl)piperidine (trans isomer)

(2) 3-[2-(3-Carboxypropyl)-3-oxo-2,3-dihydropyridazin-6-yl]-2-phenylpyrazolo[1,5-a]pyridine (3) (2R)-1-[3-(2-Phenylpyrazolo[1,5-a]pyridin-3-yl) acryloyl]-2-(carboxymethyl)piperidine (trans isomer)

(4) 3-[2-(2-Carboxymethyl-1-cyclohexenyl)-3-oxo-2,3-dihydropyridazin-6-yl]-2-phenylpyrazolo[1,5-a]pyridine The pharmaceutical composition suited for the practice of this invention may be the bulk of pyrazolopyridine compound (I), inclusive of its salt, as such or a solid, semisolid or liquid pharmaceutical preparation containing said pyrazolopyridine compound (I) or salt thereof as an active ingredient in an organic or inorganic carrier or vehicle suited for rectal, oral or parenteral (subcutaneous, intravenous, intramuscular, etc.) administration or for inhalation. The active ingredient, thus, can be compounded with various nontoxic, pharmaceutically acceptable carriers which are generally used in the production of tablets, pellets, troches, capsules, suppositories, aerosols, powders for inhalation, solution, emulsion, suspension and/or other dosage forms. Furthermore, where necessary, various auxiliary agents, stabilizers, thickeners, coloring agents and perfumes can be used. All that is necessary is that such pharmaceutical compositions should each contain said pyrazolopyridine compound (I) or its salt in a sufficient amount to express the expected prophylactic and/or therapeutic effect on the course or status of the disease to be treated.

The pharmaceutical compositions of use in the practice of this invention can be manufactured by the technology well established in the art. Where necessary, the various routine procedures for enhancing the bioavailability of a drug can also be applied to the production according to this invention.

For application of the composition of this invention to a human being or an animal, the preferred routes of administration are intravenous (inclusive of addition to an infusion), intramuscular and oral.

The effective dose of pyrazolopyridine compound (I) for the prevention and/or treatment depends on the patient's or recipient's age and other factors but the generally recommended dosage for the treatment and/or prevention of hyperphosphatemia and the like in a human being and an animal is 0.01–100 mg/day/kg body weight for intravenous administration, 0.01–100 mg/day kg body weight for intramuscular administration and 0.01–200 mg/day/kg body weight for oral administration.

The pharmaceutical composition of this invention is useful for the prevention and/or treatment of hyperphosphatemia and secondary hyperparathyroidism and their accessory disorders or symptoms.

Among the accessory disorders or symptoms mentioned above are ectopic calcification, arteriosclerosis, renal osteodystrophia, Raynaud's syndrome, ischemic dermal necrosis, cerebrovascular disorders, ischemic heart diseases, arrhythmia, cardiac valve disease, renal amyloidosis, red eye, dermal pruritus, hyperlipemia, hyperglycemia, hypertriglyceridemia, renal anemia, renal parameters to be improved, alopecia, sexual dysfunction, atrophy of gonad, paramenia and infertility.

For demonstrating the usefulness of this invention, the pharmacological data generated with a representative compound are presented below.

INVESTIGATIONAL COMPOUND (1) 3-[2-(3-Carboxypropyl)-3-oxo-2,3-dihydropyridazin-6-yl]-2-phenylpyrazolo[1,5-a] pyridine

[Hereinafter Referred to as Test Compound (1)]

Method

Male inbred Dahl S/sea rats (sodium chloride-sensitive hypertensive rats) were purchased at 5 weeks of age. At 7 weeks of age, administration of the drug and supply of 8% NaCl-food (Oriental Yeast) were started.

The test compound (1) was suspended in 0.5% MC/water and administered in a dose of 3.2 mg/kg daily for 6 consecutive weeks (provided that on Saturdays and Sundays the medicated food prepared as follows was supplied). The 0.5% MC was given to a control group and for normal feeding. The dose volume was 5 ml/kg.

(Medicated Food)

Test compound (1) was comminuted in an agate mortar and mixed into the rodent powdery food (MF, Oriental yeast) at the level of 0.005% (corresponding to 3.2 mg/kg/day) (NaCl was also added at 8% level).

On the last day of experiment, blood was drawn from the abdominal aorta of the animal under ether anesthesia and the serum was separated and subjected to biochemical tests (with Hitachi 7150 Model).

Results

The blood phosphorus concentration (mg/dl) values were as follows.

TABLE 1

| Control group | 8.5 ± 0.40 |
|---|---|
| Compound (1) group | 6.2 ± 0.25* |

*Significantly different from control at 1% level

The blood calcium concentration (mg/dl) values were as follows.

TABLE 2

| Control group | $10.4 \pm 0.13$ |
|---|---|
| Compound (1) group | $9.5 \pm 0.14$* |

*Significantly different from control at 1% level

It will be apparent from the above data that the blood phosphorus level could be depressed by administration of test compound (1) which is an adenosine antagonist, thus endorsing the effect of this invention.

Administration of test compound (1) did not cause elevation of blood calcium, concentration, suggesting that it is free from the adverse effects of calcium preparations. The above test results suggest the efficacy of adenosine antagonists in the prevention and treatment of hypercalcemia as well.

What is claimed is:

1. A method for the prevention and/or treatment of hyperphosphatemia or secondary hyperparathyroidism, inclusive of accessory disorders and symptoms thereof, which comprises administering a pharmaceutical composition which comprises an adenosine antagonist compound or a salt thereof as an active ingredient to a human being or an animal.

2. A method for the prevention and/or treatment as claimed in claim 1 wherein the adenosine antagonist is an adenosine $A_1$ antagonist.

3. A method for the prevention and/or treatment as claimed in claim 2 wherein the adenosine $A_1$ antagonist is a pyrazolopyridine compound of the general formula (I) or its salt:

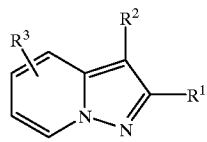

(I)

wherein $R^1$ is lower alkyl, aryl which may have one or more substituents which maintain effectiveness of said compound or a heterocyclic group;

$R^2$ is a group of the formula:

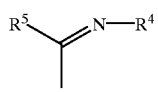

where $R^4$ is protected amino group or hydroxy group and $R^5$ is hydrogen atom or lower alkyl group; cyano group; a group of the formula:

where $R^6$ is acyl group, and
A is lower aliphatic hydrocarbon group which may have one or more substituents which maintain effectiveness of said compound;
an amidated carboxy group;
an unsaturated heterocyclic group which may have one or more substituents which maintain effectiveness of said compound;
amino group; or protected amino group; and $R^3$ is hydrogen atom, lower alkyl group, lower alkoxy group or halogen atom.

4. A method for the prevention and/or treatment as claimed in claim 3 wherein the adenosine $A_1$ antagonist is a pyrazolopyridine compound of the general formula:

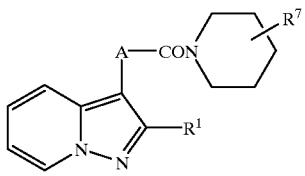

wherein $R^1$ is aryl group, $R^7$ is acyl(lower)alkyl group or a hydroxy(lower)alkyl group, and A is lower alkenyl group.

5. A method for the prevention and/or treatment as claimed in claim 4, wherein the adenosine $A_1$ antagonist is the compound described in claim 4 wherein $R^1$ is phenyl group, and $R^7$ is carboxy(lower)alkyl group.

6. A method for the prevention and/or treatment as claimed in claim 5 wherein the adenosine $A_1$ antagonist is 1-[3-(2-phenylpyrazolo-[1,5-a]pyridin-3-yl)acryloyl]-2-(carboxymethyl)piperidine.

7. A method for the prevention and/or treatment as claimed in claim 3 wherein the adenosine $A_1$ antagonist is a pyrazolopyridine compound of the general formula:

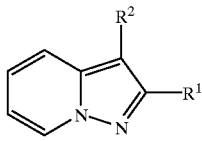

wherein $R^1$ is aryl group, and $R^2$ is dihydropyridazinyl group having acyl(lower)alkyl group and oxo group; dihydropyridazinyl group having cyclo(lower)alkyl group substituted by acyl(lower)alkyl or acyl(lower)alkylidene and oxo group; or dihydropyridazinyl group having cyclo(lower)alkenyl group substituted by acyl(lower)alkyl or acyl(lower)alkylidene and oxo group.

8. A method for the prevention and/or treatment as claimed in claim 7 wherein the adenosine $A_1$ antagonist is the compound described in claim 7 wherein $R^1$ is phenyl group, and $R^2$ is 3-oxo-2,3-dihydropyridazinyl group having carboxy(lower)alkyl group or 3-oxo-2,3-dihydropyridazinyl group having cyclo(lower)alkenyl group substituted by carboxy(lower)alkyl.

9. A method for the prevention and/or treatment as claimed in claim 8 wherein the adenosine $A_1$ antagonist is 3-[2-(3-carboxypropyl)-3-oxo-2,3-dihydropyridazin-6-yl]-2-phenylpyrazolo[1,5-a]pyridine.

10. A method for the prevention and/or treatment as claimed in claim 8 wherein the adenosine $A_1$ antagonist is 3-[2-(2-carboxymethyl-1-cyclohexenyl)-3-oxo-2,3-dihydropyridazin-6-yl]-2-phenylpyrazolo[1,5-a]pyridine.

* * * * *

UNITED STATES PATENT AND TRADEMARK OFFICE
CERTIFICATE OF CORRECTION

PATENT NO. : 6,303,624 B1
DATED : October 16, 2001
INVENTOR(S) : Nomura et al.

It is certified that error appears in the above-identified patent and that said Letters Patent is hereby corrected as shown below:

<u>Title page,</u>
Item [45] and the Notice information should read:

-- [45] Date of Patent:   *Oct. 16, 2001

-- (*)   Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

Signed and Sealed this

Twenty-ninth Day of April, 2003

JAMES E. ROGAN
*Director of the United States Patent and Trademark Office*